United States Patent
Zhang et al.

(10) Patent No.: US 12,371,413 B2
(45) Date of Patent: Jul. 29, 2025

(54) METHOD FOR PREPARING 2-IODOHETEROCYCLIC ARYL ETHER AT ROOM TEMPERATURE

(71) Applicant: SOOCHOW UNIVERSITY, Suzhou (CN)

(72) Inventors: Shilei Zhang, Suzhou (CN); Wenjing Zhu, Suzhou (CN); Yanwei Hu, Suzhou (CN); Liang Yu, Suzhou (CN); Jingjing Gui, Suzhou (CN); Yuanrui Jiang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 291 days.

(21) Appl. No.: 18/012,586

(22) PCT Filed: Feb. 22, 2021

(86) PCT No.: PCT/CN2021/077325
§ 371 (c)(1),
(2) Date: Dec. 22, 2022

(87) PCT Pub. No.: WO2022/174468
PCT Pub. Date: Aug. 25, 2022

(65) Prior Publication Data
US 2023/0348413 A1 Nov. 2, 2023

(51) Int. Cl.
*C07D 333/32* (2006.01)

(52) U.S. Cl.
CPC .................. *C07D 333/32* (2013.01)

(58) Field of Classification Search
CPC .................................... C07D 333/32
See application file for complete search history.

(56) References Cited

FOREIGN PATENT DOCUMENTS

| | | |
|---|---|---|
| CN | 111620841 A | 9/2020 |
| CN | 112300154 A | 2/2021 |
| CN | 112979612 A | 6/2021 |
| WO | 2012028676 A1 | 3/2012 |

OTHER PUBLICATIONS

Fan Yang et al., "Facile synthesis of dihaloheterocycles via electrophilic iodocyclization" Tetrahedron 67 (2011) 10147-10155 (Sep. 3, 2011).
Fan Yang et al. "Facile synthesis of 3,4-diiododihydrothiophenes via electrophilic iodocyclization" Tetrahedron Letters 52 (2011) 936-938 (Dec. 23, 2010).

*Primary Examiner* — Golam M Shameem
(74) *Attorney, Agent, or Firm* — SZDC Law PC

(57) ABSTRACT

Disclosed is a method for preparing a 2-iodoheterocyclic aryl ether at room temperature, including adding an alkali metal hydride and a phenol to a solvent, then adding a diiodoheterocyclic aromatic hydrocarbon, and performing a reaction at 0-100° C., so as to obtain a 2-iodoheterocyclic aryl ether product. In the coupling process of the present invention, no transition metal catalyst needs to be added, and no metal pollution will be caused to the product. The product of the present invention can be used as an organic synthesis raw material for a further reaction, and can also be used as an additive flame retardant reagent to improve the flame retardant performance of plastics.

7 Claims, 1 Drawing Sheet

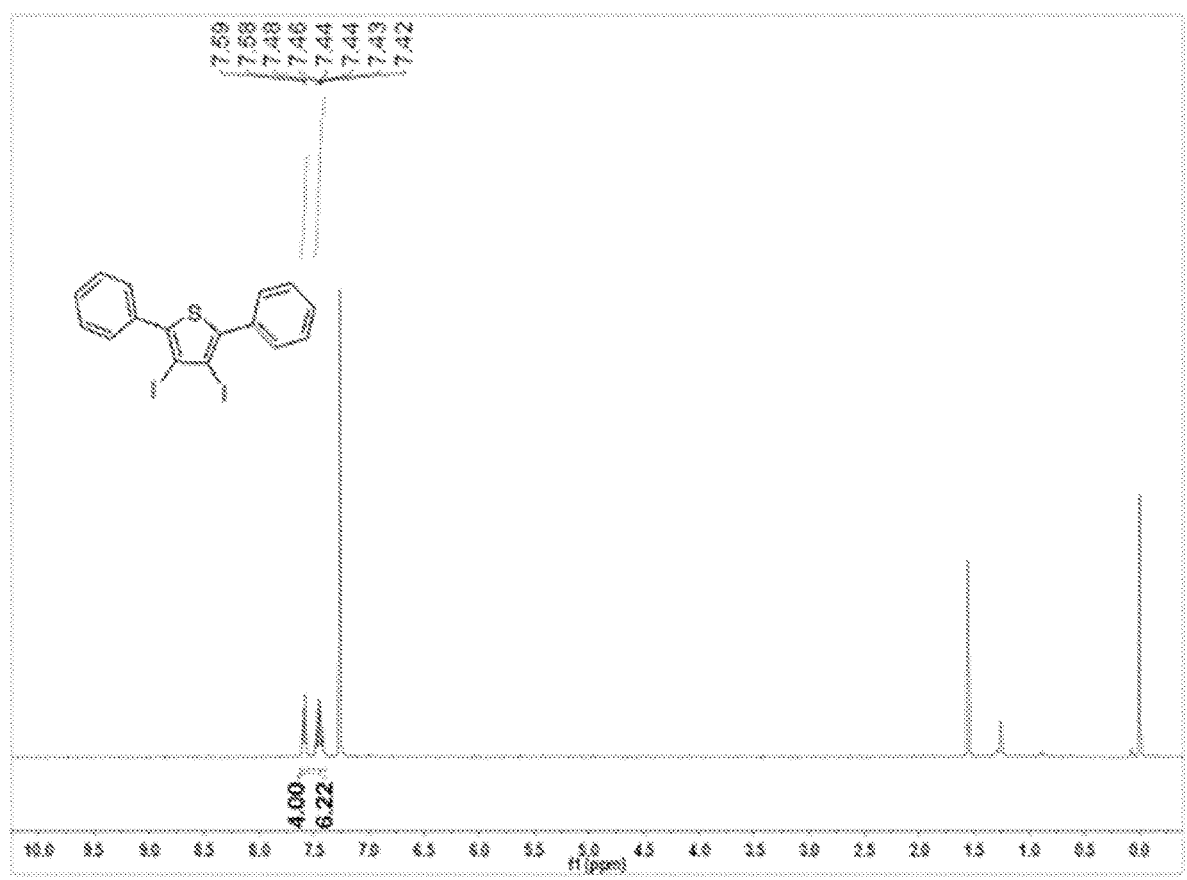

METHOD FOR PREPARING 2-IODOHETEROCYCLIC ARYL ETHER AT ROOM TEMPERATURE

This application is the National Stage Application of PCT/CN2021/077325, filed on Feb. 22, 2021, which is incorporated by reference for all purposes as if fully set forth herein.

TECHNICAL FIELD

The present invention belongs to the technical field of organic synthesis, and particularly relates to a method for preparing 2-iodo heterocyclic aromatic ether by a coupling reaction of an aryne intermediate generated by ortho-iodine halide under the action of alkali metal hydride and phenol.

BACKGROUND OF INVENTION

The average concentration of oxygen in the air is 21%, and the plastic with the general oxygen index below 21 is flammable plastic, the plastic with the general oxygen index of 22-27 is self-extinguishing plastic, the plastic with higher general oxygen index is flame-retardant plastic and the pure plastic needs to be added with a flame retardant to be non-flammable. The halogenated flame retardant refers to a type of flame retardant containing halogen elements. Because of the low C—X bond energy, the halogenated flame retardant is easy to decompose under the action of high temperature, the reaction absorbs heat to reduce the surface temperature of the material, and meanwhile, the flame-retardant high-density gas HX can expel air to form a protective layer on the surface of the asphalt to prevent the combustion of the resin. Four elements in the halogenated flame retardant: fluorine, chlorine, bromine and iodine have flame retardance, and the flame-retardant effect is sequentially enhanced according to the order of fluorine, chlorine, bromine and iodine. Because the fluorine-containing flame retardant cannot effectively capture free radicals and the iodine-containing flame retardant has poor stability, the halogenated flame retardant used at present mainly comprises chlorine and bromine. For the products with low flame-retardant requirements, the development of new iodine-containing compounds has industrial value.

Technical Problems

The present invention provides a method for synthesizing 2-iodo-heterocyclic aromatic ether in one step at room temperature; the ortho-iodine halide is used for the first time to absorb halogen atoms of another molecule of ortho-iodine halide under the action of alkali metal hydride to form a 2-iodo-heterocyclic aromatic ether product, and the obtained product can be used for flame retardance of resin.

Technical Solution

The technical means of synthesizing the 2-iodo-heterocyclic aromatic ether is to mix alkali metal hydride, phenol and 2-iodo-heterocyclic aromatic hydrocarbon in a solvent and stirred conventionally to obtain the product. The specific technical scheme is as follows: a method for preparing 2-iodo-heterocyclic aromatic ether at room temperature comprises the following steps: 2-iodo-heterocyclic aromatic hydrocarbon reacts with phenol in the presence of alkali metal hydride to obtain 2-iodo-heterocyclic aromatic ether; preferably, adding alkali metal hydride and phenol into a solvent, then adding 2-iodo-heterocyclic aromatic hydrocarbon to react at 0-100° C. to obtain the 2-iodo-heterocyclic aromatic ether.

In the present invention, the phenol is phenol, substituted phenol or heterocyclic phenol.

In the present invention, the alkali metal hydride is sodium hydride, potassium hydride and calcium hydride, preferably sodium hydride and potassium hydride, more preferably sodium hydride.

In the present invention, the solvent is one or several of DMF (N, N-dimethylformamide), DMA (N, N-Dimethylacetamide), THF (tetrahydrofuran), 2-MeTHF (2-methyltetrahydrofuran), DME (ethylene glycol dimethyl ether), MTBE (methyl tert-butyl ether), diethyl ether, DMSO, NMP (N-methyl-2-pyrrolidone), toluene, preferably DMA and THF, more preferably a mixture of DMA and THF.

In the present invention, the mole ratio of the phenol to the 2-iodo-heterocyclic aromatic hydrocarbon to the alkali metal hydride is 1:(0.1-10):(1.2-10); preferably 1:(0.5-5):(1.5-5); more preferably 1:(1-3):(2-4); most preferably 1:1.5:3.

In the technical scheme, the reaction temperature is 10-50° C., preferably the room temperature; the reaction time is 0.2-10 hours, preferably 0.5-2 hours.

The preparation method of the 2-iodo-heterocyclic aromatic ether of the present invention has the following advantages:

1) transition metal catalysts are not needed to be added in the coupling process, so that metal pollution to products is avoided;
2) the method can be carried out at room temperature, it has high functional group compatibility, and it solves the problem that the coupling reaction of the existing metal catalysis into the aromatic ether needs to be carried out at higher temperature;
3) the reaction is simple, the reagent is cheap, and the required cost is low;
4) it can prepare the products that are not easily prepared by other methods, such as products with iodine in both aromatic rings.

In the present invention, the chemical structure of 2-iodoheterocyclic aromatic hydrocarbon is as follows:

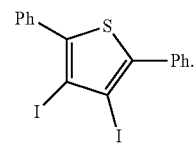 [SMILES: Ic1c(-c2ccccc2)sc(-c2ccccc2)c1I]

In the present invention, the chemical structure of phenol is $Ar^2OH$.

In the present invention, the chemical structure of 2-iodoheterocyclic aromatic ether is as follows:

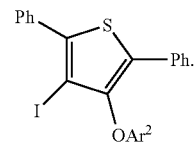

In the present invention, Are is benzene, naphthalene, pyridine, quinoline, pyrimidine, thiophene, and the like.

Beneficial Effects

The coupling reaction of phenol and iodide does not need any catalyst, the operation is simple, the by-product of the reaction is only sodium iodide, and no toxic substances are generated; the 2-iodo-heterocyclic aromatic ether prepared by the present invention can be obtained by only one-step mild reaction without excessive coupling products, and is superior to all existing methods.

BRIEF DESCRIPTION OF THE DRAWINGS

FIG. 1 shows the nuclear magnetic spectrum of product 1i.

EMBODIMENT OF THE PRESENT INVENTION

The technical scheme of the invention is as follows: An alkali metal hydride was suspended in a solvent, the phenol was added, and then 2-iodo heterocyclic aromatic hydrocarbon was added for reaction for 0.2-10 hours at room temperature. After that, water was added to terminate the reaction, and the solvent was extracted and evaporated to dry for column chromatography purification to obtain the product of 2-iodo-heterocyclic aromatic ether; the reaction of the present invention does not need inert atmosphere and catalyst, and after adding materials to the reaction flask, the reaction can be carried out by capping it; the specific operation and purification are conventional techniques.

The starting materials involved in the present invention are all commercially available products; the specific preparation and testing methods used are existing techniques.

Example of Synthesis

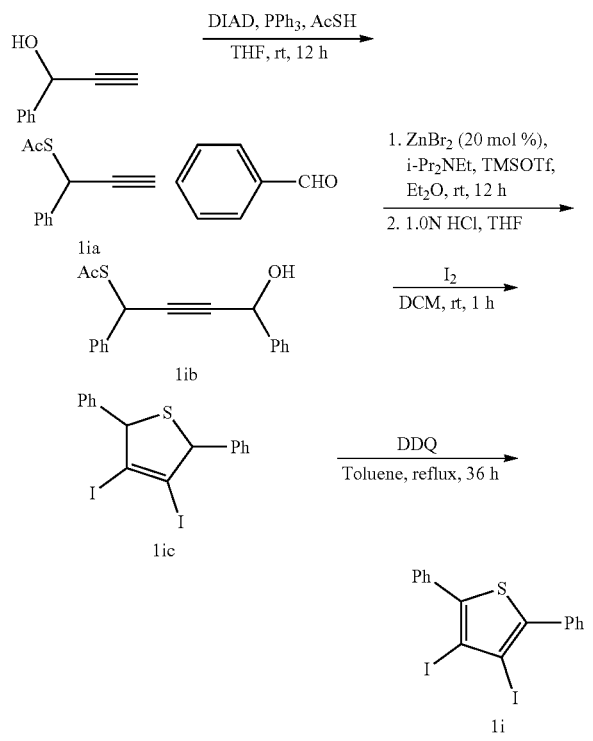

Triphenylphosphine (39 mmol, 10.48 g) was dissolved in THF (80 mL), stirred at 0° C., and diisopropyl azodicarboxylate (DIAD) (39 mmol, 7.9 mL) was added and stirred at 0° C. for 1 h. 1-phenyl-2-propyn-1-alcohol (30 mmol, 4.0 g) and thioacetic acid (39 mmol, 2.86 mL) was added in THF (20 mL), and the temperature was raised to the room temperature for 12 h reaction. It was evaporated to dryness and the residue was diluted with hexane (80 mL), filtered, evaporated to dryness and purified by column chromatography to obtain the black oil product 1ia with the yield of 57%.

Zinc dibromide (702 mg, 2.7 mmol) was suspended in ether (81 mL) under nitrogen protection and 1ia (2.39 g, 12.5 mmol), diisopropylethylamine (4.15 mL, 27 mmol), benzaldehyde (2.7 mL, 27 mmol) and TMSOTf (2.93 mL, 16.2 mmol) were dropwise in sequentially. The reaction mixture was stirred at room temperature for 12 hours. The solid was filtered through diatomite, and the filtrate was concentrated and then diluted with THF (30 mL). 1.0M HCl (45 mL) was added and stirred for 1 hour, extracted with EA, washed with water and saturated $NaHCO_3$. It was evaporated to dryness and purified by column chromatography to obtain the yellow oil product 1ia with the yield of 51%.

$I_2$ (9 mmol, 2.28 g) was added to a solution of 1ib (3 mmol, 888 mg) dichloromethane (30 mL) and the resulting mixture was stirred at room temperature for 1 hour. The reaction mixture was diluted with dichloromethane and washed with saturated sodium thiosulfate. It was evaporated to dryness and purified by column chromatography to obtain the yellow solid product 1ic with the yield of 44%.

DDQ (3 mmol, 681 mg) was added to a solution of 1ic (1 mmol, 489 mg) methylbenzene (20 mL) and the resulting mixture was stirred at refluxing temperature for 36 hours. It was filtered, evaporated to dryness and purified by column chromatography to obtain the yellow solid product 1i with the yield of 85%. Refer to FIG. 1 for nuclear magnetic spectrum, $^1$H NMR (400 MHz, $CDCl_3$) δ 7.59-7.56 (m, 4H), 7.48-7.42 (m, 6H).

Example 1

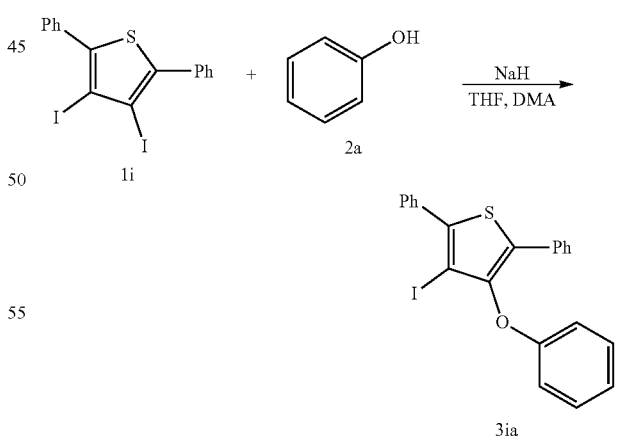

Sodium hydride (60% in oil, 36 mg, 0.9 mmol, 3 eq.) was suspended in THF (1 mL), and it was conventionally stirred and added into a solution of phenol 2a (28 mg, 0.3 mmol, 1 eq.) in DMA (0.3 mL), and then it was stirred for 10 minutes at room temperature. After that, it was added to a solution of 1i (151 mg, 0.45 mmol, 1.5 eq.) in THF (0.2 mL) for reaction for 1 hour at room temperature. After the reaction was completed, water was added for quenching and it was extracted with ethyl acetate three times and the organic layers were combined and dried with sodium sulfate, evaporated to dryness and purified by column chromatography to obtain the product of iodo-aromatic ether 3ia with the yield of 94%. $^1$H NMR (400 MHz, CDCl$_3$) δ 7.71 (m, 4H), 7.56-7.20 (m, 8H), 7.11-6.88 (m, 3H). LR-MS (ESI): m/z 455.1 [M+H]$^+$.

Example 2

Sodium hydride (60% in oil, 36 mg, 0.9 mmol, 3 eq.) was suspended in THF (1 mL), and it was conventionally stirred and added into a solution of phenol 2a (28 mg, 0.3 mmol, 1 eq.) in DMA (0.3 mL), and then it was stirred for 10 minutes at room temperature. After that, it was added to a solution of 1i (151 mg, 0.45 mmol, 1.5 eq.) in THF (0.2 mL) for reaction for 1 hour in ice-water bath. After the reaction was completed, water was added for quenching and it was extracted with ethyl acetate three times and the organic layers were combined and dried with sodium sulfate, evaporated to dryness and purified by column chromatography to obtain the product of iodo-aromatic ether 3ia with the yield of 54%.

Example 3

Sodium hydride (60% in oil, 36 mg, 0.9 mmol, 3 eq.) was suspended in THF (1 mL), and it was conventionally stirred and added into a solution of phenol 2a (28 mg, 0.3 mmol, 1 eq.) in DMA (0.3 mL), and then it was stirred for 10 minutes at room temperature. After that, it was added to a solution of 1i (151 mg, 0.45 mmol, 1.5 eq.) in THF (0.2 mL) for reaction for 1 hour at 50° C. After the reaction was completed, water was added for quenching and it was extracted with ethyl acetate three times and the organic layers were combined and dried with sodium sulfate, evaporated to dryness and purified by column chromatography to obtain the product of iodo-aromatic ether 3ia with the yield of 95%.

Example 4

Potassium hydride (0.9 mmol, 3 eq.) was suspended in THF (1 mL), and it was conventionally stirred and added into a solution of phenol 2a (28 mg, 0.3 mmol, 1 eq.) in DMA (0.3 mL), and then it was stirred for 10 minutes at room temperature. After that, it was added to a solution of 1i (151 mg, 0.45 mmol, 1.5 eq.) in THF (0.2 mL) for reaction for 1 hour at room temperature. After the reaction was completed, water was added for quenching and it was extracted with ethyl acetate three times and the organic layers were combined and dried with sodium sulfate, evaporated to dryness and purified by column chromatography to obtain the product of iodo-aromatic ether 3ia with the yield of 25%.

Example 5

Calcium hydride (0.9 mmol, 3 eq.) was suspended in THF (1 mL), and it was conventionally stirred and added into a solution of phenol 2a (28 mg, 0.3 mmol, 1 eq.) in DMA (0.3 mL), and then it was stirred for 10 minutes at room temperature. After that, it was added to a solution of 1i (151 mg, 0.45 mmol, 1.5 eq.) in THF (0.2 mL) for reaction for 1 hour at room temperature. After the reaction was completed, water was added for quenching and it was extracted with ethyl acetate three times and the organic layers were combined and dried with sodium sulfate, evaporated to dryness and purified by column chromatography to obtain the product of iodo-aromatic ether 3ia with the yield of 12%.

Application example: Iodo-aromatic ether 3ia, epoxy resin E44 and ethylenediamine in a weight ratio of 0.5:10:1 were used as starting materials, a process of curing at room temperature for 12 hours and curing at 60° C. for 1.5 hours was adopted, and the prepared sample was tested according to ASTM D2863 to get the oxygen index of 23.6; an epoxy resin E44 and ethylenediamine in a weight ratio of 10:1 was used as a comparison to get the oxygen index of 20.7.

Compared with the prior art, the present invention can obtain the 2-iodo-heterocyclic aromatic ether only by stirring commercial O-dihalobenzene (at least one of which is iodine) and phenol for a period of time at room temperature under the action of alkali metal hydride, and is obviously superior to the existing methods in terms of synthesis efficiency and cost; the product can be used as a non-reactive flame retardant to improve the flame-retardant property of pure resin.

The invention claimed is:

1. A method for preparing a 2-iodo-heterocyclic aromatic ether at room temperature comprising following steps: reacting a 2-iodo-heterocyclic aromatic hydrocarbon with a phenol in the presence of an alkali metal hydride to obtain the 2-iodo-heterocyclic aromatic ether, wherein the 2-iodo-heterocyclic aromatic ether is

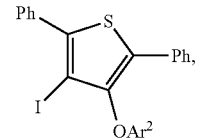

and Ar$^2$ is benzene, naphthalene, pyridine, quinoline, pyrimidine, or thiophene.

2. The method for preparing the 2-iodo-heterocyclic aromatic ether at room temperature according to claim 1, comprising adding the alkali metal hydride and the phenol into a solvent, then adding the 2-iodo-heterocyclic aromatic hydrocarbon to obtain the 2-iodo-heterocyclic aromatic ether.

3. The method for preparing the 2-iodo-heterocyclic aromatic ether at room temperature according to claim 2, wherein the solvent is one or more selected from the group consisting of DMF, DMA, THF, 2-MeTHF, DME, MTBE, diethyl ether, DMSO, NMP, and toluene.

4. The method for preparing the 2-iodo-heterocyclic aromatic ether at room temperature according to claim 1, wherein the alkali metal hydride is sodium hydride, potassium hydride or calcium hydride; the phenol is unsubstituted phenol, a substituted phenol or a heterocyclic phenol.

5. The method for preparing the 2-iodo-heterocyclic aromatic ether at room temperature according to claim 1, wherein a mole ratio of the phenol to the 2-iodo-heterocyclic aromatic hydrocarbon to the alkali metal hydride is 1:(0.1-10):(1.2-10).

6. The method for preparing the 2-iodo-heterocyclic aromatic ether at room temperature according to claim 5, wherein a mole ratio of the phenol to the 2-iodo-heterocyclic aromatic hydrocarbon to the alkali metal hydride is 1:(0.5-5):(1.5-5).

7. The method for preparing the 2-iodo-heterocyclic aromatic ether at room temperature according to claim 1, wherein a reaction temperature is 10-50° C.; a reaction time is 0.2-10 hours.

* * * * *